United States Patent [19]

Frigerio et al.

[11] Patent Number: 4,956,369
[45] Date of Patent: Sep. 11, 1990

[54] 2-DITHIOALKYL-DIHYDROPYRIDINES AND PHARMACEUTICAL COMPOSITIONS CONTAINING THEM

[75] Inventors: Marco Frigerio; Carmelo A. Gandolfi; Sergio Tognella, all of Milan, Italy

[73] Assignee: Boehringer Biochemia Robin S.p.A., Milan, Italy

[21] Appl. No.: 333,815

[22] Filed: Apr. 6, 1989

Related U.S. Application Data

[63] Continuation of Ser. No. 136,988, Dec. 23, 1987, abandoned.

[30] Foreign Application Priority Data

Dec. 24, 1986 [IT] Italy ............... 22881 A/86

[51] Int. Cl.$^5$ ............... C07D 401/12; A61K 31/505
[52] U.S. Cl. ............... 514/274; 546/321; 546/318; 546/316; 546/157; 546/281; 546/194; 546/256; 546/257; 546/283; 546/284; 546/276; 546/277; 546/278; 546/268; 546/270; 546/271; 546/286; 546/322; 544/360; 544/131; 544/333; 544/324; 544/262; 544/287; 544/318
[58] Field of Search ............... 546/256, 257, 316, 318, 546/286, 322, 321, 270, 218, 286, 157, 281, 194, 283, 284, 276, 277, 268, 271; 544/318, 360, 131, 333, 324, 262, 287; 514/269, 333, 334, 336, 341, 344, 352, 355, 356, 343, 252, 255, 233, 342, 256, 340, 342, 275, 248, 338, 339, 265, 312

[56] References Cited

U.S. PATENT DOCUMENTS

| | | | |
|---|---|---|---|
| 4,284,634 | 8/1981 | Satu | 546/286 |
| 4,492,703 | 1/1985 | Goldman et al. | 546/139 |
| 4,532,248 | 7/1985 | Franckowick et al. | 514/302 |

FOREIGN PATENT DOCUMENTS

| | | |
|---|---|---|
| 0095450 | 11/1983 | European Pat. Off. . |
| 0123850 | 11/1984 | European Pat. Off. . |
| 0169009 | 1/1986 | European Pat. Off. . |
| 0200524 | 11/1986 | European Pat. Off. . |
| 2120251 | 11/1983 | United Kingdom ............... 546/321 |

OTHER PUBLICATIONS

The Merk Index 9th Edition pp. 7853-7854.
Reid, E. E. Organic Chemistry of Bivalent Sulfur Vol. III (1960) p. 368.
Chemical Abstracts 96:162501y, Angelova, and Original Article (Angelova, God. Sofii. Univ., Khim. Fak. 1977 (Published 1981).
Bossert et al., Angew. Chem. Int. Ed. Eng. 20,762–769 (1981).
Chemical Abstract 105:226293w, Cupka et al., and Original Article (Cupka et al., S nth. Commun. 1986, 16(5), 529–534).
Franckowiak et al., European Journal of Pharmacology 114 (1985) 223–226.
Seidel, Second European Seminar and Exhibition on Computer Aided Molecular Designs, Basel, Oct. 17–18, 1985.
Hof et al., Journal of Cardiovascular Pharmacology, 1985, 689–693.
Schachtele et al., Archives of Pharmacology, 1987, 340–343.
Honn et al., Proceedings of the Society for Experimental Biology in Medicine, 174, 16–19 (1983).
Onoda et al., Cancer Letters, 30(1986) 181–188.
Onoda et al., Hemostatic Mechanisms and Metastasis, pp. 207–226, The Hague, 1984.
Burger Medicinal Chem. 2nd Edition Interscience Publishers Inc. N.Y. 1960, pp. 565–601.
Onoda et al., Thrombosis Research, vol. 34, pp. 367–378, 1974.
Chemical Abstracts, vol. 103, No. 9, Sep. 2, 1985, p. 636, Abstract No. 71161j; and Chemical Abstract Service, Registry Handbook, Number Section, 1985 Supplement, p. 2812RN, RN97669-55-1.

Primary Examiner—Jane T. Fan
Attorney, Agent, or Firm—Armstrong, Nikaido, Marmelstein Kubovcik & Murray

[57] ABSTRACT

Compounds of formula I

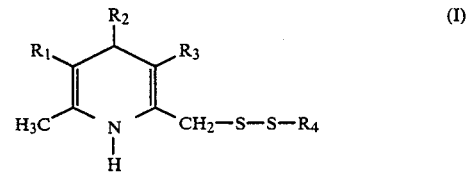

wherein
$R_1$ and $R_3$, which are the same or different, are alkoxycarbonyl, acetyl, cyano, nitro, benzoyl or amino-carbonyl groups,
$R_2$ is differently substituted aryl or heteroaryl group;
$R_4$ is a $C_1$-$C_{12}$ alkyl group optionally substituted by amino, alkoxyl, amine, etc. groups; alkenyl, or alkinyl groups; optionally substituted aryl or heteroaryl groups.

Compounds I are useful as antihypertensives in human therapy.

5 Claims, No Drawings

2-DITHIOALKYL-DIHYDROPYRIDINES AND PHARMACEUTICAL COMPOSITIONS CONTAINING THEM

This application is a continuation of application Ser. No. 136,988 filed Dec. 23, 1987 now abandoned.

The present invention concerns 2-dithio-alkyl-1,4-dihydropyridines, a method for their preparation and pharmaceutical compositions containing them.

The compounds of the invention have the following general formula I

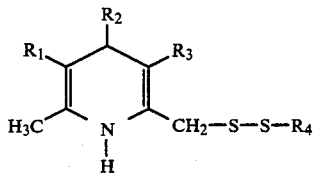 (I)

wherein $R_1$ is acetyl benzoyl, cyano, nitro, a $COOR_5$ or a $CONR_6R_7$ group;

$R_2$ is:

(a) a phenyl group that can be unsubstituted or substituted by one or more $C_1$–$C_6$-alkoxy, halo-$C_1$–$C_6$-alkyl, halo-$C_1$–$C_4$-alkoxy, halogen, nitro, cyano, $C_1$–$C_6$alkoxycarbonyl, $C_1$–$C_4$-alkylthio groups;

(b) pentafluorophenyl;

(c) α and β-naphtyl;

(d) a 5 or 6 membered heterocyclic ring;

$R_3$ is a $COOR_5$ group;

$R_4$ is a $C_1$–$C_{12}$ alkyl, $C_2$–$C_6$ alkenyl, $C_2$–$C_5$ alkynyl group, phenyl, mono-or-bicyclic heterocycle, phenyl-$C_1$–$C_4$-alkyl or heterocyclyl-$C_1$–$C_4$-alkyl, said groups being optionally substitued by hydroxy, amino, monoalkylamino, dialkylamino, $C_1$–$C_4$-alkoxy, $C_1$–$C_6$-acylamino, carboxy, $C_1$–$C_4$-alkoxycarbonyl, nitro, cyano, $C_1$–$C_3$-alkylthio, trifluoromethyl, $C_1$–$C_3$-alkyl groups; the monoheterocyclic residues having 5 or 6 members each or biheterocyclic residues each of the cycle thereof having 5 or 6 members;

$R_5$ is a $C_1$–$C_6$-alkyl chain, that may optionally be substituted by hydroxy, amino, monoalkylamino, dialkylamino $C_1$–$C_6$-alkoxy, $C_3$–$C_6$-alkenyl groups or optionally substituted aryl groups;

$R_6$ and $R_7$, which are the same or different, are hydrogen, $C_1$–$C_6$-alkyl, benzyl or aryl.

Pharmaceutically acceptable salts, optical antipodes, i.e. the single enantiomers, diastereoisomers and mixtures thereof are also included in the scope of the present invention.

Pharmaceutically acceptable salts of compounds of the invention are those with pharmaceutically acceptable acids and bases.

PCT/WO/87/00445, German patent No. 2658183, and the european patent application Nos. 200524, 222598, 206747, 221720, 232025 disclose 1,4-dihydropyridines having in position 2 a differently substituted methylthio group.

It is obvious that the compounds of the invention are structurally different from compounds of said prior-art patent. In particular the disulfide group (—S—S—) is chemically different from thioether group (—S—), due to electronic and reactivity characteristics (see for example Houben-Weyl, Methoden der Organischen Chemie, G. Thieme Verlag, Stuttgart, 1955, Vol. 9, chapters 3 and 5).

Moreover, the differences of behaviour "in vivo" of the two disulphide and thioether systems, are known for instance comparing the metabolism of cysteine and methionine, (A. L. Lehninger "Biochimica" Zanichelli Milan, 1980, chap. 20).

In the compounds of the invention the alkyl, alkenyl, acyloxy, acylthio and acylamino groups may have both linear or branched chain.

A halo-$C_1$–$C_6$-alkyl group is preferably a trihalomethyl and in particular trifluoromethyl group.

A halo-$C_1$–$C_4$-alkoxy groups is preferably difluoromethoxy.

A $C_1$–$C_6$-alkyl group is preferably methyl, ethyl, isopropyl or ter-butyl.

An aryl group is preferably phenyl.

A heteroaryl group is preferably an α or β-pyridyl.

A monoalkylamino group is preferably methyl, ethyl-, isopropyl- or benzylamino.

A dialkylamino group is preferably dimethyl-, diethyl-, N-methyl-N-benzylamino.

A dialkylamino group is more preferably a group whose alkyl substituents are a part of an heterocyclic ring, such as pyrrolidin-1-yl, piperidin-1-yl, piperazin-1-yl, 4-substituted-piperazin-1-yl, imidazol-1-yl, morpholin-4-yl.

When $R_2$ is a 5 or 6 membered heterocyclic ring it is preferably pyridyl, furanyl, thienyl; when $R_4$ is a heterocyclic ring it may be both heteromonocyclic and selected in the group consisting of N, S and O.

Preferred examples of heteromonocyclic residues are α-, β- and γ-pyridyl, tetrahydrofuryl, thienyl, β-pyridyl-N-oxide, 3-hydroxy- pyridyl; 2- and 4-pyrimidinyl; 1H-1,2,4-triazol-3-yl; 1H-1,2,4-triazol-5-yl; 2-thiazolyl, 1-methyl-tetrazol-5-yl, 2-methyl-1,3,4-triazol-5-yl; 5-amino-1,3,4-thiadiazol-2-yl, 2-amino-1,3,4-triazol-5-yl, 2-hydantoinyl, 2-imidazolinyl, 4-methyl-imidazol-2-yl, 1-phenyl-1H-tetrazol-5-yl, 4,5-diphenyl-4-oxazolin-2-yl, 4-phenoxymethyl-5-carboxyimidazol-2-yl and their esters with $C_1$–$C_4$ alcohols, 1,4,5,6-tetrahydro-pyrimidin-2-yl, 4-substituted-imidazol-2-yl, 5-carboxy-4-substituted-imidazol-2-yl, pyrimidin-2-yl and their derivatives with methyl, amino, oxo and/or carboxy groups in positions 4 or 6 of the pyrimidine, pyrimidin-6-yl, 2,6-diamino-pyrimidin-4-yl, tetrahydropyran-2-yl, (3,4,5-triacetoxy-6-acetoxymethyl)-tetrahydropyran-2-yl, 5-carboetoxy-4-oxo-pyrimidin-2-yl,6-propyl-4-hydroxy-pyrimidin-2-yl and 6-propyl-4-amino-pyrimidin-2-yl.

Preferred examples of heterobicyclic residues are 4-(3H)-quinazolin-4-one-2-yl, 2-quinazolinyl, 4-aminopyrazol[3,4-d]pyrimidin-2-yl, 6-purinyl, 6,8-dihydroxy-2-purinyl, benzothiazol-2-yl, benzooxazol-2-yl, benzimidazol-2-yl and derivatives thereof, substituted in the benzene ring by alkoxy or halo-substituents, quinolyn-2-yl, 7-trifluoromethylquinolin-4-yl.

The aryl and heterocyclic $R_4$ residues may be bound to the sulphur atom by means of an alkyl chain, that should preferably be a $C_1$–$C_4$ chain.

When $R_4$ is a mono- or polysubstituted chain, or a $C_1$–$C_{12}$ alkyl chain, it will preferably be the residue of $C_1$–$C_{12}$ alkyl thiols, such as 3-phenyl-propan-2-thiol, 3-cyclohexyl-propan-1-thiol, 3-cyclopentyl-propan-1-thiol, 2-propen-1-thiol, 2-propin-1-thiol, 2-mercapto-1-ethanol and ethers or thioethers thereof, such as 2-methoxyethan-1-thiol, 2-ethoxy-ethan-1-thiol, 2-propoxy-ethan-1-thiol, 2-isopropoxy-ethan-1-thiol, 3-phenoxy-propan-1-thiol, 2-methylthio-ethan-1-thiol, 2-ethylthio-ethan-1-thiol, etc., 3-mercapto-1,2-propandiol and 1,2-acetates, 2-furyl-methanthiol, 2-(2-furyl)-ethan-1-thiol, 2(2-thienyl)-ethan-1-thiol, 2-(3-thienyl)-ethan-1-thiol, 2-(4-methyl-5-thiazolyl)-ethan-1-thio1,2-(imidazol-1-yl)-ethan-1-thiol, 2-($\beta$-pyridyl)-ethan-1-thiol, 3-(imidazol-(pyrrol-1-yl)-ethan-1-thiol, 2-(2,5-dimethyl-pyrrol-1-yl)-ethan-1-thiol, 3-(2,5-dimethyl-pyrrol-1-yl)-ethan1-thiol, 2-(2,5-dimethyl-pyrrol-1-yl)-propan-1-thiol, alkylamino-alkylthiols like 2-dimethylamino-ethan-1-thiol, 2-diethylamino-ethan-1-thiol, 2-butylamino-ethan-1-thiol, 2-(N-morpholin)-ethan-1-thiol, 2-(pyrrolidinyl)-ethan1-thiol, 2-(N-piperidinyl)-ethan-1-thiol, 2-(4'-N-substituted-piperazin-1-yl)-ethan-1-thiol, aminoalkylthiols like cysteamine, homocysteamine, 4-aminobutan-1-thiol and derivatives thereof, wherein the amino group is protected by BOC, acylamide or cycloimide, 3-amino-3-monoalkylamino and 3-dialkylaminopropan-1-thiols, mercaptoacids like tioglycolic, thiolactic and thiomalic acids and derivatives thereof, such as esters, amides or nitriles, $\alpha$-aminoacids containing thiol groups like cysteine, homocysteine, and polypeptides obtained starting from these aminoacids, for example glutathione;

$R_5$ is preferably methyl, ethyl or isopropyl.

Specific examples of compounds of the invention are shown in Table I:

(1) reaction of a dihydropyridine of formula II

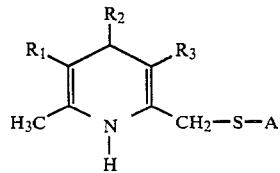
(II)

Wherein $R_1$, $R_2$ and $R_3$ are as above defined and A is a leaving group (chlorine, bromine, mesylate, tosylate, brosylate) or the cation of an alkaline or alkaline-earth metal, with a compound of formula III $R_4$—S—B wherein $R_4$ is as above defined and B is a leaving group (chlorine, bromine, mesylate, tosylate, brosylate) or the cation of an alkaline or alkaline-earth, provided that when A is a leaving group, B is a metal cation and vice versa.

The reaction of a compound of formula II with a compound of formula III is carried out in an inert solvent such as an alcohol, e.g. methanol, ethanol, isopropanol; an ether, e.g. tetrahydrofuran, dioxane; an aro-

TABLE I

| N° | $R_1$ | $R_2$ | $R_3$ | $R_4$ |
|---|---|---|---|---|
| 1 | —CO$_2$Et | mNO$_2$C$_6$H$_4$ | —CO$_2$Et | —C$_6$H$_5$ |
| 2 | —CO$_2$Me | mClC$_6$H$_4$ | —CO$_2$Et | —C$_6$H$_5$ |
| 3 | —CN | mNO$_2$C$_6$H$_4$ | —CO$_2$Et | —C$_6$H$_5$ |
| 4 | —NO$_2$ | mNO$_2$C$_6$H$_4$ | —CO$_2$Et | —C$_6$H$_5$ |
| 5 | —CO$_2$Et | mNO$_2$C$_6$H$_4$ | —CO$_2$Et | —C$_2$H$_5$ |
| 6 | —CO$_2$Me | mClC$_6$H$_4$ | —CO$_2$Et | —C$_4$H$_9$ |
| 7 | —CO$_2$C$_3$H$_7$-i | o SCH$_3$C$_6$H$_4$ | —CO$_2$Me | —CH$_2$—CH=CH$_2$ |
| 8 | —CO$_2$Me | pF—C$_6$H$_4$ | —CO$_2$C$_3$H$_7$-i | —CH$_2$—C≡CH |
| 9 | —CO$_2$Me | o CF$_3$C$_6$H$_4$ | —CO$_2$Me | —CH$_2$—CH(OH)CH$_2$—OH |
| 10 | —CO$_2$Me | mNO$_2$—C$_6$H$_4$ | —CO$_2$Et | —CH$_2$CH$_2$NH—COCH$_3$ |
| 11 | —CO$_2$Et | mCH$_3$SC$_6$H$_4$ | —CO$_2$Me | —CH$_2$CH$_2$NH$_2$ |
| 12 | —CO$_2$Me | mNO$_2$C$_6$H$_4$ | —CO$_2$Et | —CH$_2$CH$_2$NH$_2$ |
| 13 | —CO$_2$Me | $\beta$-pyridyl | —CO$_2$Et | —CH$_2$CH(NH$_2$)—COOH |
| 14 | —CO$_2$Et | o-Cl—C$_6$H$_4$ | —CO$_2$Me | —CH$_2$-furyl |
| 15 | —CO$_2$CH$_2$CH$_2$OCH$_3$ | mCF$_3$C$_6$H$_4$ | —CO$_2$Me | —CH$_2$-pyrimidinyl |
| 16 | —CO$_2$Me | mNO$_2$C$_6$H$_4$ | —CO$_2$Me | N-methylimidazolyl |
| 17 | —CO$_2$Me | C$_6$H$_5$ | —CO$_2$Me | benzoxazolyl |
| 18 | —CO$_2$Et | mNO$_2$C$_6$H$_4$ | —CO$_2$Et | o (COOH)C$_6$H$_4$— |
| 19 | —COCH$_3$ | C$_6$H$_5$ | —CO$_2$Me | —CH$_2$CH$_2$OCOCH$_3$ |
| 20 | —CO$_2$C$_3$H$_7$-i | 2,3-di-Cl—C$_6$H$_3$ | —CO$_2$Et | —CH$_2\phi$ |
| 21 | —CO$_2$Me | mNO$_2$C$_6$H$_4$ | —CO$_2$Et | —CH$_2\phi$ |
| 22 | —CO$_2$Me | mNO$_2$C$_6$H$_4$ | —CO$_2$Et | -$\phi$ |

The compounds of the invention are obtained by a process comprising:

matic solvent, e.g. benzene, toluene, 1,3-dichlorobenzene; a chlorinated solvent e.g. chloroform, dichloromethane, 1,2-dichloroethane or a mixture thereof, at a temperature ranging from −80° C. to 0° C. for reaction times ranging from a few minutes to some hours.

The compounds of formula I obtained may optionally be submitted to salification, acylation, optical resolution processes, in order to obtain other compounds of formula I.

The compounds of formula II wherein A is a cation of an alkaline or alkaline-earth metal are prepared preferably "in situ" from compounds of formula IV

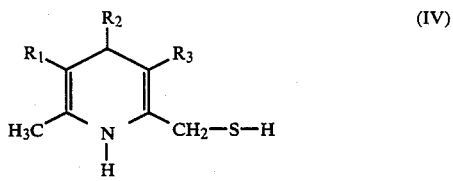

wherein $R_1$, $R_2$ and $R_3$ are as above indicated, by treatment with a strong bases, such as, for instance, sodium hydrate, potassium hydrate, sodium ethylate, magnesium ethylate, calcium hydride, potassium ter-butylate in an inert solvent, such as an alcohol, e.g. ethanol, methanol, isopropanol, an ether like dioxane, tetrahydrofuran, 1,2-dimethoxyethane, the resulting solutions being useful as such.

Compounds of formula II wherein A is a halogen (chlorine, bromine) are prepared "in situ" by reaction of compounds of formula IV with an halogenating agent, such as N-chloro-succinimide, N-bromo-succinimide, chlorine or bromine in an inert solvent such as chloroform, carbon tetrachloride, dioxane, at temperatures ranging from −30° C. to the room temperature.

The obtained solutions are preferably used as such.

The compounds of formula II wherein A is a leaving group such as mesylate, tosylate and brosylate are obtained by reacting a dihydropyridine of formula V

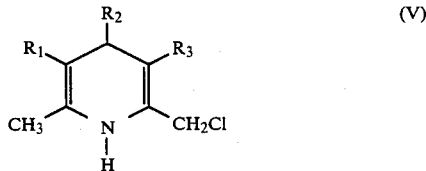

Wherein $R_1$, $R_2$ and $R_3$ are as above defined, with a compound of formula VI

wherein $R_8$ is methyl, phenyl, p-methylphenyl, p-bromophenyl and $M^+$ is the cation of an alkaline or alkaline earth metal.

The reaction is carried out in an inert solvent such as dimethylformamide, dimethylsulphoxide, an alcohol, a chlorinated solvent or an ether by means of condensation of equimolecular quantities of compounds V and VI or with a slight molar excess of the latter at a temperature ranging from −20° C. to the solvent's reflux temperature for periods ranging from a few minutes to 48 hours.

The compounds of formula III are known and/or easily available or the may be prepared by known methods.

The compounds of formula IV are prepared according to the methods disclosed in PCT/WO/87/00445 whereas compounds V are disclosed in EP 212340.

The compounds of formula VI are known or preparable by known methods, as described e.g. in Houben Weyl, Methoden der Organischen Chemie, G. Thieme, Verlag, Stuttgart, Vol. 11-E2, pages 1112 and followings.

The compounds of the invention show "in vivo" a prolonged antihypertensive activity and a calcium-antagonist activity "in vitro".

The compounds of the invention can decrease the mean blood pressure when they are administered per as to spontaneously hypertensive rats.

The compounds of the invention are useful for treatment of hypertensive diseases of various etiology.

The compounds may be administered in various manners to achieve the desired effect. The compounds may be administered alone or in the form of pharmaceutical preparations to the patient to be treated either orally or parenterally, i.e., intravenously or intramuscularly. The formulation of suitable pharmaceutical compositions can be carried out by the skilled man according to the common knowledge in the art, such as that disclosed in the "Remington's Pharmaceutical Sciences" Handbook, Mack Publishing Company, U.S.A. The amount of compound administered will vary with the severity of the hypertension, and the mode of administration. For the oral administration, the effective amount is from about 0.01 mg/kg of body weight per day to about 10 mg/kg body weight per day and preferably from about 0.05 mg/kg body weight per day to about 5 mg/kg body weight per day.

For parenteral administration the antihypertensively effective amount of compound is from about 0.001 mg/kg body weight per day up to about 5 mg/kg body weight per day and preferably from about 0.01 mg/kg body weight per day up to about 2 mg/kg body weight per day.

For oral administration a unit dosage may contain, for example, from 0.50 to 100 mg of the active ingredient. For parenteral administration a unit dosage may contain, for example, from 0.05 to 70 mg of the active ingredient. Since the compounds of the invention generally possesses a long lasting duration of action, they might be conveniently administered once or twice a day, however, repetitive daily administrations may be, at least in some instances, desirable and will vary with the conditions of the patient and the mode of administration. As used herein, the term "patient" is taken to mean a warm blooded animal, humans included.

For oral administration the compounds can be formulated into solid or liquid preparations such as capsules, pills, tablets, troches, powders, solutions, suspensions or emulsions. The solid unit dosage forms can be a capsule which can be of the ordinary gelatin type, either hard or soft, containing for example lubricants and inert fillers, such as lactose, sucrose and cornstarch.

In another embodiment the compounds of the invention can be tabletted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Examples of oils which can be used in these preparations are those of mineral petroleum, animal, vegetable or synthetic origin. For example, peanut oil, soybean oil and mineral oil. In general, water, saline, aqueous dextrose and related sugar solutions, ethanol and glycols such as propylene glycol or polyethylene glycol can be used as liquid carriers for injectable solutions.

For rectal administration the compounds are administered in the form of suppositories, admixed with conventional vehicles such as, for example, cocoa butter, wax, spermaceti, polyvinylpyrrolidone, or polyoxyethylenglycols and their derivatives.

The preferred administration route for compounds of the invention is the oral route.

The following examples illustrate but do not limit the invention.

EXAMPLE 1

A solution of 2-chloromethyl-3-carboethoxy-5-carbomethoxy-4-(m-nitrophenyl)-6-methyl-1,4-dihydropyridine (11.4 g) and potassium thiotosylate (R. B. Woodward et al. J. Org. Chem. 36, 1137–1139, 1971) (10 g) in dimethylformamide (70 ml) is stirred for 18 hours under nitrogen atmosphere, then it is poured in water (700 ml) and extracted with ethyl acetate (3×100 ml). The organic phase is washed with a sodium bicarbonate solution (3×50 ml) and water (3×50 ml), dried and evaporated in vacuum.

The residue (20 g) is purified by chromatography on silica-gel (400 g; eluent hexane-ethyl acetate 80/20). The purified products is triturated with ethyl ether to give 8 g of 2-(4-methyl-phenyl-sulfonylthio)-methyl-2-carboethoxy-5-carbomethoxy 4-(m-nitrophenyl)-6-methyl-1,4-dihydropyridine, m.p. 118°–120° C.

Using in the above process, potassium or sodium thiotosylate and a 2-chloromethyl-1,4-dihydropyridine, the following 2-(4 methyl phenyl-sulfonylthio)methyl-6-methyl 1, 4-dihydropyridines were obtained:
  3-carboethoxy-5-carbomethoxy 4 (m-chlorophenyl);
  3-carboethoxy-5-nitro-4-(m-nitrophenyl);
  3,5-dicarboethoxy-4-(m-nitrophenyl);
  3-carboisopropoxy-5-carbomethoxy-4-p-fluorophenyl);
  3,5-dicarbomethoxy-4-(m-nitrophenyl).

EXAMPLE 2

A solution of sodium thiophenate (0,73 g) in methanol (15 ml) is dropped into a solution of 2-(4-methylphenyl-sulphonylthio)-methyl- 3-carbomethoxy-5-carboethoxy-4-(m-nitrophenyl)-6-methyl-1,4-dihydropyridine (3 g) in methanol (18 ml) and dichloromethane (9 ml) under nitrogen atmosphere at −60° C.

When the addition is over, the solution is poured in iced water (200 ml) and extracted with ethyl acetate (3×50 ml). The organic phase is washed with bicarbonate (5%, 3×15 ml), dried and evaporated under vacuum. The residue is triturated with isopropyl ether to give 2 g of 2-(phenyldithio)methyl-3-carboethoxy-5-carbomethoxy-4-(m-nitrophenyl)-6-methyl-1,4-dihydropyridine, m.p. 132°–133° C.

Using in the above procedure a suitable 2-(4-methylphenyl-sulfonylthio)-methyl-1,4-dihydropyridine and a thiol selected in the group of thiophenol, ethylmercaptan, butylmercaptan, 2-N-acetylcysteamine, cysteamine, the following 6-methyl-1,4-dihydropyridines were obtained
  2-(phenyl dithio)-methyl-3-carboethoxy-5-carbomethoxy 4-(m-chlorophenyl);
  2-(phenyl-dithio)-methyl 3-carboethoxy-5-cyano-4-(m-nitrophenyl);
  2-(phenyl-dithio)-methyl-3 carboethoxy-5-nitro-4-(m-nitrophenyl);
  2-(phenyl-dithio)-3,5 dicarboethoxy-4-(m-nitrophenyl);
  2-(2-acetamido-ethyl-dithio)-methyl-3-carboethoxy-5- carbomethoxy-4-(m-nitrophenyl)-; m.p. 133°–136° C.;
  2-(ethyl-dithio)-methyl-3,5-dicarboethoxy-4-(m-nitrophenyl);
  2-(butyl-dithio)-methyl-3-carboethoxy-5-carbomethoxy-4-(m-chlorophenyl);
  2-(amino-ethyl-dithio)-3-carboethoxy-5-carbomethoxy-4-(m-nitrophenyl);
  2-(2-amino-ethyl-dithio)-methyl-3-carbomethoxy-5-carboethoxy-4-(m-methylthiophenyl);
  2-(2-amino-2-carboxy-ethyl-dithio)-methyl-3,5-dicarboethoxy-4-(m-nitrophenyl);
  2-(2,3-dihydroxy-propyl-dithio)-methyl-3,5-dicarbomethoxy-4-(o-trifluoro-methyl-phenyl);
  2-(propin-3-yl-dithio)-methyl-5-carbomethoxy-3-carboisopropoxy-4-(p-fluoro-phenyl);
  2-(propen-3-yl-dithio)-methyl-3-carbomethoxy-5-carboisopropoxy-4-(o-methylthiophenyl);
  2-(2-furylmethyl-dithio)-methyl-3 carbomethoxy-5-carboethoxy-4-(o-chlorophenyl);
  2-(2-acetoxy-ethyl-dithio)-methyl-3,5-dicarboethoxy-4-phenyl;
  2-[(1-methyl-imidazol-2-yl)-dithio)]-methyl-3,5-dicarbomethoxy-4-(m-nitrophenyl).

EXAMPLE 3

A chloroform suspension (15 ml) of thiosalycilic acid (0.75 g) and N-chlorosuccinimide (0.70 g) is heated at 50° C. for 15 minutes, then it is cooled to room temperature and a solution of 2-mercaptomethyl-3,5-di-carboethoxy-4-(m-nitrophenyl)-6-methyl-1,4-dihydropyridine (1.95 g) in chloroform (20 ml) is added therewith. After 30 minutes the reaction mixture is diluted with chloroform (30 ml), washed with water (3×20 ml), sodium bicarbonate (5%, 1×10 ml), again with water (3×10 ml), dried (Na ) and evaporated.

The solid obtained is triturated with ethyl ether to give a 2-[(2-carboxy-phenyl)dithio]-methyl-3,5-dicarboethoxy-4-(m-nitrophenyl)-6-methyl-1,4-dihydropyridine (1.5 g).

NHR (COCl$_3$) δ 1.00–1.20 (6H, m); 2.10 (3H, s); 3.80–4.10 (6H, m); 4.90 (1H, s); 7.00–8.10 (9H, m); 8.90 (1H, s).

EXAMPLE 4

Some drops of a thiophenol solution (5.5 g) in dichloromethane (25 ml) are added at room temperature to a solution, under nitrogen atmosphere, of N-chlorosuccinimide (6.8 g) in dichloromethane (25 ml). The solution is then warmed until exothermic reaction starts; the heating bath is removed and the reaction mixture is refluxed by dropping the chloroformic thiophenol solution.

The solution is then refluxed for further 15 minutes and cooled to −25° C., adding thereafter in 2 hours a solution of 2-mercaptomethyl-3,5-dicarboethoxy-4-(m-nitrophenyl) 6-methyl-1,4-dihydropyridine (18 g) and triethylamine (5 g) in dichloromethane (100 ml), at a temperature from −25° C. to −20° C.

The mixture is stirred at −25° C. for 30', then water is added (80 ml). The two phases are separated and the organic one is washed with water (3×30 ml), dried and concentrated under vacuum.

The obtained residue is purified by chromatography on silica gel (500 g, eluente isopropyl ether). 2.5 g of 2-(phenyl-dithio)-methyl-3,5-dicarboethoxy-4-(m-nitrophenyl)-6-methyl-1,4-dihydropyridine are obtained, m.p. 85°–87° C.

Using the same procedure the following compounds were also obtained: 2-(phenyldithio)methyl-3-carboethoxy-5-carbomethoxy-4-(m-nitrophenyl)-6-methyl-1,4-dihydropyridine, 2-(2-pyrimidyl-dithio)methyl-3-carbomethoxy-5-methoxyethoxycarbonyl-4-(m-trifluoro-methylphenyl)-6-methyl-1, 4-dihydropyridine;

2-(benzyl-dithio)-methyl-3-carboethoxy-5-carbomethoxy-4-(m-nitrophenyl)-6-methyl-1,4-dihydropyridine.

We claim:

1. A compound of formula I wherein

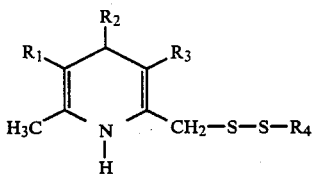

(I)

$R_1$ is acetyl, benzoyl, cyano, nitro, a $COOR_5$ or a $CONR_6R_7$ group;

$R_2$ is selected from the group consisting of m-nitrophenyl, o-chlorophenyl, m-chlorophenyl, o-trifluoromethylphenyl, p-fluorophenyl, phenyl, o-methylthiophenyl, m-methylthiophenyl, pyridyl, and 2,3-dichlorophenyl;

$R_3$ is a $COOR_5$ group;

$R_4$ is selected from the groups $C_1$–$C_{12}$ alkyl, $C_2$–$C_6$ alkenyl, $C_2$–$C_5$ alkynyl, phenyl heterocyclic moiety, phenyl-$C_1$–$C_4$-alkyl, or $C_1$–$C_4$-alkyl substituted by a heterocyclic moiety, said groups being optionally substituted by hydroxy; amino; monolalkylamino selected from the group consisting of ethylamino, isopropylamino and benzylamino; dialkylamino selected from the group consisting of dimethylamino, diethylamino, N-methyl-N-benzylamino, pyrrolidin-1-yl, piperidin-1-yl, piperazin-1-yl and morpholin-4-yl; $C_1$–$C_4$-alkoxy; $C_2$–$C_6$-acylamino; carboxy; $C_1$–$C_4$-alkoxy carbonyl; nitro; cyano; $C_1$–$C_3$-alkylthio; trifluoromethyl; and $C_1$–$C_3$-alkyl, said heterocyclic moiety being selected from the group consisting of:

(A) α-pyridyl; β-pyridyl; γ-pyridyl; tetrahydrofuryl; thienyl; α-pyridyl-N-oxide; 3-hydroxy-pyridyl; 2-pyrimidinyl; 4-pyrimidinyl; 1H-1,2,4-triazol-3-yl; 1H-1,2,4-triazol-5-yl; 2-thiazolyl; 1-methyl-tetrazol-5-yl; 2-methyl-1,3,4-triazol-5-yl; 5-amino-1,3,4-thiadiazol-2-yl; 2-amino-1,3,4-triazol-5-yl; 2-hydantoinyl; 2-imidazolinyl; 4-methyl-imidazol-2-yl; 1-phenyl-1H-tetrazol-5-yl;4,5-diphenyl-4-oxazolin-2-yl; 4-phenoxymethyl-5-carboxyimidazol-2-yl and esters thereof with $C_1$–$C_4$ alcohols; 1,4,5,6-tetrahydro-pyrimidin-2-yl; pyrimidin-2-yl unsubstituted or substituted with methyl, amino, oxo and/or carboxy groups in positions 4 or 6 of the pyrimidine ring; pyrimidin-6-yl; 2,6-diamino-pyrimidin-4-yl; tetrahydropyran-2-yl; (3,4,5-triacetoxy-6-acetoxymethyl)-tetrahydropyran-2-yl; 5-carboxyethoxy-4-oxo-pyrimidin-2-yl; 6-propyl-4-hydroxy-pyrimidin-2-yl; 6-propyl-4-aminopyrimidin-2-yl;

(B) 4-(3H)-quinazolin-4-one-2-yl; 2-quinoazolinyl; 4-aminopyrazol pyrimidin-2-yl; 6-purinyl; 6,8-dihydroxy-2-purinyl; benzothiazol-2-yl; benzooxazol-2-yl; benzimidazol-2-yl unsubstituted or substituted in the benzene ring with alkoxy or halogen substituents; quinolyn-2-yl; and 7-trifluoromethylquinolin-4-yl;

$R_5$ is a $C_1$–$C_6$-alkyl chain, that may optionally be substituted by hydroxy; amino; monoalkylamino selected from the group consisting of methylamino, ethylamino, isopropylamino and benzylamino; dialkylamino selected from the group consisting of dimethylamino, diethylamino, N-methyl-N-benzylamino, pyrrolidin-1-yl, piperidin-1-yl, piperazin-1-yl and morpholin-4-yl; $C_1$–$C_6$-alkoxy; $C_3$–$C_6$-alkenyl; or phenyl;

$R_6$ and $R_7$, which are the same or different, are hydrogen, $C_1$–$C_6$-alkyl, benzyl or phenyl, its enantiomer, diastereoisomer, or a pharmaceutically acceptable salt thereof.

2. A compound as in claim 1, wherein said heterocyclic moiety in $R_4$ is selected from the group consisting of α-pyridyl; β-pyridyl; γ-pyridyl; tetrahydrofuryl; thienyl; α-pyridyl-N-oxide; 3-hydroxy-pyridyl; 2-pyrimidinyl; 4-pyrimidinyl; 1H-1,2,4-triazol-3-yl; 1H-1,2,4-triazol-5-yl; 1-methyl-tetrazol-5-yl; 2-methyl-1,3,4-triazol-5-yl; 2-amino1,3,4-triazol-5-yl; 2-hydantoinyl; 2-imidazolinyl; 4-methyl-imidazol-2-yl; 1-phenyl-IH-tetrazol-5-yl; 4-phenoxymethyl-5-carboxyimimazol-2-yl and esters thereof with $C_1$–$C_4$ alcohols; 1,4,5,6-tetrahydro-pyrimidin-2-yl; pyrimidin-2-yl unsubstituted or substituted with methyl, amino, oxo and/or carboxy groups in positions 4 to 6 of the pyrimidine ring; pyrimidin-6-yl; 2,6-diaminopyrimidin-4-yl; tetrahydropyran-2-yl; (3,4,5-triacetoxy-6-acetoxymethyl)-tetrahyropyran-2-yl; 5-carboethoxy-4-oxo-pyrimidin-2-yl; 6-propyl-4-hydroxy-pyrimidin-2-yl; and 6-propyl-4-aminopyrimidin-2-yl.

3. A compound according to claim 1 wherein $R_4$ is selected in the group consisting of ethyl, butyl, allyl, propargyl, 2-aminoethyl, 2-acetylaminoethyl, 1-(2, 3-dihydroxy)propyl, 1-(2-amino-2-carboxy)ethyl, benzyl, acetoxyethyl, 2-furyl-methyl, 2-pyrimidinyl, 2-(1-methyl)-imidazolyl.

4. A pharmaceutical composition for anti-hypertensive treatment, comprising a compound of any one of claims 1, 3 or 2, and a pharmaceutical vehicle.

5. A method for treatment of hypertension, comprising administering to a subject suffering from hypertension an anti-hypertensive effective amount of a compound of any one of claims 1, 3 or 2.

* * * * *